United States Patent
Hartl et al.

(10) Patent No.: US 6,388,104 B1
(45) Date of Patent: May 14, 2002

(54) 4-METHYLENE-1,3-DIOXOLANES HAVING FUNCTIONAL GROUPS

(75) Inventors: Helmut Hartl; Rainer B. Frings; Gerwald F. Grahe, all of Berlin (DE)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 09/679,066

(22) Filed: Oct. 5, 2000

(30) Foreign Application Priority Data

Oct. 6, 1999 (EP) .............................. 99119160

(51) Int. Cl.$^7$ ............................. C07D 317/12

(52) U.S. Cl. ................ 549/450; 549/453; 549/454

(58) Field of Search ................ 549/450, 453, 549/454

(56) References Cited

U.S. PATENT DOCUMENTS 2,455,733 A * 7/1948 Radcliffe et al. ............. 260/84

OTHER PUBLICATIONS

Meister, et al, 1982, Synthesis, 9, 758–760.*

* cited by examiner

Primary Examiner—T. A. Solola
Assistant Examiner—Andrea D'Souza Small
(74) Attorney, Agent, or Firm—Armstrong, Westerman & Hattori, LLP

(57) ABSTRACT

Novel 4-methylene-1,3-dioxolanes of the general formula I

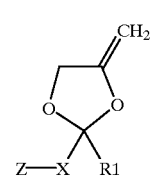

in which R1 denotes hydrogen or alkyl, X denotes a single bond, $C_1$–$C_{18}$ alkylene, cycloalkylene, arylalkylene, —$CH_2(OCH_2CH_2)_n$— or —$CH_2(OCH(CH_3)CH_2)_n$—, in which n is an integer from 1 to 100, and Z means a functional group selected from among —OH, —COOR' or —OCOR', in which R' denotes hydrogen or $C_1$–$C_8$ alkyl, are described, as are a process for the production thereof and the intermediates used in this process.

13 Claims, No Drawings

4-METHYLENE-1,3-DIOXOLANES HAVING FUNCTIONAL GROUPS

FIELD OF THE INVENTION

This invention relates to novel 4-methylene-1,3-dioxolanes having functional groups, which is easy applicable to UV curable inks, coatings as a reactive thinner or a crosslinking agent, to a process for the production thereof and to the intermediates used in this process.

BACKGROUND OF THE INVENTION

Commercially available vinyl ethers are based on base-catalysed addition of acetylene onto alcohols under pressure. The resultant compounds contain the structural element $H_2C=CH-OR$ and have been used industrially for many years. These compounds have attracted particular attention in cationic and photocationic polymerisation as, due to their electron-rich double bond, they are generally highly reactive compounds.

However, users always complain that volatile, strong-smelling components are formed during crosslinking which, at elevated concentration, are irritant and thus problematic on occupational hygiene grounds. Comprehensive precautions are thus required on occupational safety and health protection grounds which not only entail considerable costs for users, but also put up the prices of their products.

It has been known for some time that one of the principal components of these unwanted volatile secondary products is acetaldehyde, which is produced in a secondary reaction of vinyl ether with ambient moisture. T. Moriguchi et al., *Macromolecules* 1995, 28, 4334–4339, have reported a possible reaction pathway.

Various approaches to solving this problem have been discussed for some time. From an economic standpoint, the most promising approach would seem to be to rearrange readily available allyl ethers to yield isopropenyl ethers on noble metal catalysts (J. V. Crivello, U.S. Pat. No. 5,486, 545, Jan. 23, 1996). However, this approach overlooks the fact that, during cationic and photocationic polymerisation, isopropenyl ethers may also enter into a secondary reaction with water, analogous to that of the commercial vinyl ethers, resulting in the formation of propionaldehyde. Isopropenyl ethers are thus also incapable of satisfying the requirement for emission-free crosslinking. Open-chain vinyl ethers are in principle incapable of achieving this as it is always possible for them to give rise to volatile cleavage products in the presence of moisture.

Cyclic vinyl ethers, on the other hand, such as for example 2,3-dihydrofurans and 2,3-dihydropyrans, are virtually ideal vinyl ethers. While they may indeed also enter into secondary reactions with water during photocationic reactions, no volatile cleavage products are formed, as the irritant aldehyde component remains firmly attached to the molecule. However, these heterocyclic compounds, if they are to have a suitable degree of substitution which permits further conversion, are complex to synthesise, such that relatively large quantities have not hitherto been industrially available at reasonable cost.

In contrast, the class of 4-methylene-1,3-dioxolanes is much more straightforwardly available.

U.S. Pat. No. 2,445,733, Jul. 21, 1945, describes the first attempts to crosslink 4-methylene-1,3-dioxolanes. However, depending upon the metal ion, the Friedel-Crafts catalysts which are used give rise to reddish-brown coloured masses, but not to solvent-resistant networks. Using an alcoholic solution of zinc chloride (H. Orth, *Angew. Chem.* 1952, 64, 544–553) brought about some improvement, but the polymerisations performed were markedly exothermic and sometimes proceeded explosively on addition of the catalyst. One positive feature which may be noted, however, is that the resultant networks have considerable surface hardness and, consequently, good workability.

It has recently been found that 4-methylene-1,3-dioxolanes are also photocationically active. K. D. Belfield and F. B. Abdelrazzaq, *Macromolecules* 1997, 30, 6985–88 accordingly describe photocationic crosslinking of 2,2'-(1, 4-phenylene)bis(4-methylene-1,3-dioxolane) with 2-phenyl-4-methylene-1,3-dioxolane. Both monomers are, however, of an aromatic nature, i.e. they have aromatic substituents in position 2. It is, however, now known that 4-methylene-1,3-dioxolanes which have a 2,2-diphenyl- or 2-phenyl-2-alkyl substitution polymerise with elimination of the ketone component (R. S. Davidson, G. J. Howgate, *J. Photochem. Photobiol. A.,* 1997, 109, 185–193 and Y. Hiraguri, T. Endo, *J. Polym. Sci. Part A: Polym. Chem.* 1989, 27, 4403–4411), i.e. eliminating components of a greater or lesser degree of volatility. As a result, the requirement for emission-free crosslinking cannot be met.

It has now surprisingly been found that purely aliphatically substituted 4-methylene-1,3-dioxolanes differ fundamentally from the aromatic derivatives thereof and may be crosslinked under photocationic conditions without emissions. This is confirmed by findings in the scientific literature: 2-isopropenyl-4-methylene-1,3-dioxolane yields a linear polymer having ketone groups, wherein polymerisation proceeds exclusively by ring-opening (J. Park, N. Kihara, T. Ikeda, T. Endo, *J. Polym. Sci. Part A: Polym. Chem.* 1993, 31, 1083–1085).

The possibility of designing crosslinking systems based on 4-methylene-1,3-dioxolanes has hitherto more or less been restricted to the industrial availability of dialdehydes and diketones and the tetraacetals and tetraketals thereof. The lack of suitably substituted 4-methylene-1,3-dioxolanes is thus noticeably restricting the potential possibilities of this class of monomers.

SUMMARY OF THE INVENTION

The object of the invention is to provide novel 4-methylene-1,3-dioxolanes which have at least one further functional group, such as for example an OH group or ester group, such that further conversions are individually possible. These 4-methylene-1,3-dioxolanes should satisfy the following requirements:

(i) no elimination of acetaldehyde or propionaldehyde during crosslinking, (ii) ready availability by means of industrially straightforward operations, (iii) production from low cost basic substances available in industrial quantities, (iv) no use of costly noble metal catalysts or catalyst systems which are difficult to regenerate, (v) activity equal to or greater than commercial vinyl ethers, (vi) low vapour pressure so that there is virtually no odour nuisance.

The present invention provides 4-methylene-1,3-dioxolanes of the general formula I

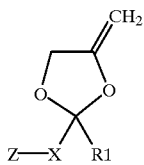

I in which R1 denotes hydrogen or alkyl, X denotes a single bond, $C_1$–$C_{18}$ alkylene, cycloalkylene, arylalkylene, —$CH_2$($OCH_2CH_2$)$_n$— or —$CH_2$($OCH(CH_3)CH_2$)$_n$—, in which n is an integer from 1 to 100, and Z means a functional group selected from among —OH, —COOR' or —OCOR', in which R' denotes hydrogen or $C_1$–$C_8$ alkyl.

DETAILED DESCRIPTION OF THE INVENTION

The 4-methylene-1,3-dioxolanes according to the invention, which may be considered 1,1-disubstituted vinyl ethers, satisfy the above stated conditions (i) to (vi). The reactivity of vinyl ethers is known approximately to follow the series $R^1R^2C$=CH—O—R<$R^1$CH=CH—O—R<$CH_2$=CH—O—R<$CH_2$=$CR^3$—O—R, i.e. the 1,1-disubstituted vinyl ethers are generally the most reactive if their substituents are not too sterically demanding (O. Nuyken, R. B. Raether, C. E. Spindler, *Macromol. Chem. Phys.* 1988, 199, 191–196).

The invention is based on the surprising observation that, despite simultaneously having an allyl structure (allyl compounds being known to have a slight tendency to polymerise), the 4-methylene-1,3-dioxolanes represented by the general formula I exhibit the elevated reactivity of 1,1-disubstituted vinyl ethers in photocationic reactions.

There follow some definitions of terms which are used in this document:

Unless otherwise stated, the term "alkyl" denotes a monovalent alkane residue of the general formula $C_nH_{2n+1}$, in which n denotes the number of carbon atoms and ranges from 1 to 18, preferably from 1 to 6.

The alkyl residues may be linear or branched.

Examples of such alkyl residues are methyl, ethyl, n-propyl, isopropyl, n-butyl, isobutyl, t.-butyl etc . . .

The term "alkylene" denotes a linear or branched, divalent hydrocarbon residue having 1 to 18 carbon atoms.

Examples of such alkylene residues are methylene, ethylene, n-propylene, isopropylene etc . . .

The term "cycloalkylene" designates a cyclic alkylene residue having 5 or 6 carbon atoms.

Examples of such cyclic alkylene residues are cyclopentanediyl and cyclohexanediyl.

The term "arylalkylene" denotes a divalent arylaliphatic residue, in which aryl denotes an aromatic hydrocarbon residue, for example phenyl, naphthyl or anthryl, and alkylene is defined as above.

According to a preferred embodiment of the 4-methylene-1,3-dioxolanes according to the invention, the functional group Z denotes an OH group or an ester group.

Particularly preferred 4-methylene-1,3-dioxolanes according to the invention are 2-methyl-2-hydroxymethyl-4-methylene-1,3-dioxolane, 2-(1-hydroxymethyl-2-methyl-propan-2-yl)-4-methylene-1,3-dioxolane, 2-methyl-2-ethoxycarbonylmethyl-4-methylene-1,3-dioxolane, 2-methyl-2-(1-cyclopentenylcarboxylic acid ethyl ester-1-yl)-4-methylene-1,3-dioxolane and 2-methyl-2-(propionic acid ethyl ester-3-yl)-4-methylene-1,3-dioxolane.

The 4-methylene-1,3-dioxolanes according to the invention are produced by a process which is characterised in that 4-chloromethyl-1,3-dioxolanes of the general formula II

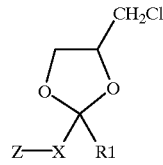

II in which R1, X and Z are defined as above, are treated with a base at a temperature of 0° C. to 150° C. and the reaction product is isolated using per se known methods.

The process is preferably performed at a temperature of 20° C. to 60° C.

Suitable bases are alkali metal and alkaline earth metal hydroxides, such as for example sodium hydroxide, potassium hydroxide or calcium hydroxide, as well as the alkali metal salts of primary, secondary and tertiary alcohols, such as for example sodium methylate, sodium ethylate or potassium tert.-butylate. When such substances are not commercially available, the corresponding alkali metals, alkali metal hydrides or alkali metal hydroxides may be dissolved in the corresponding alcohols. Potassium tert.-butylate is particularly preferred as the base.

Treatment with a base may proceed without a solvent. Generally, however, it is more advantageous to use a solvent. These may be alcohols, such as for example methanol, ethanol, isopropanol, 1-butanol or tert.-butanol, as well as ethers, such as for example dioxane, ethylene glycol dimethyl ether or tetrahydrofuran, but solvents such as dimethyl sulfoxide or DMF are also suitable. Esters of any kind are, however, less suitable as they may saponify under the reaction conditions. Particularly preferred solvents are those which are good solvents for the base used, but do not dissolve the metal chloride formed during the reaction. In this manner, isolation of the product is simplified.

The invention also provides the chloromethyl compounds of the general formula II used for the production of the 4-methylene-1,3-dioxolanes according to the invention

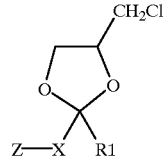

II in which R1, X and Z are defined as above.

Preferred chloromethyl compounds of the formula II are 2-methyl-2-hydroxymethyl-4-chloromethyl-1,3-dioxolane, 2-(1-hydroxymethyl-2-methylpropan-2-yl)-4-chloromethyl-1,3-dioxolane, 2,4-bis(chloromethyl)-2-methyl-1,3-dioxolane, 2-methyl-2-ethoxycarbonylmethyl-4-chloromethyl-1,3-dioxolane, 2-methyl-2-(1-cyclopentenylcarboxylic acid ethyl ester-1-yl)-4-chloromethyl-1,3-dioxolane, 2,4-bis(chloromethyl)-1,3-dioxolane and 2-methyl-2-(propionic acid ethyl ester-3-yl)-4-chloromethyl-1,3-dioxolane.

The chloromethyl compounds II are simply obtainable by reacting functional aldehydes and ketones of the general structure III

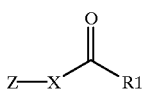

in which R1, X and Z are defined as above, with 3-chloro-1,2-propanediol. This reaction is catalysed by acids, such as for example p-toluenesulfonic acid or sulfuric acid. In the case of some reactive aldehydes, catalysis may be entirely dispensed with. Examples of compound III which may be mentioned are: hydroxyacetone, 2,2-dimethyl-3-hydroxypropanal, 3-acetyl-1-propanol, 1-hydroxy-2-methyl-3-butanone, p-hydroxybenzylacetone,, chloroacetone, glyoxylic acid, pyruvic acid, acetoacetic ester and very particularly 3,3-dialkyl-substituted acetoacetic ester, laevulinic acid, bromo- or chloroacetaldehyde dimethyl acetal.

The water arising during the reaction is removed by distillation, wherein the presence of a suitable entraining agent has an advantageous effect. Water-immiscible solvents, such as for example toluene, chloroform or cyclohexane are very particularly suitable for this purpose. It is immaterial whether the reagents dissolve homogeneously in the entraining agent or whether they form two phases. If no entraining agent is used, it is advisable to apply a slightly reduced pressure when removing the water, provided that the reagents used permit this. If a diacetal is used as the starting material, the resultant alcohol may readily be removed by distillation.

The functional 4-methylene-1,3-dioxolanes produced according to the invention, very particularly the compounds having OH and ester groups, may subsequently be converted, for example using suitable diols and diesters, into bis- and poly(4-methylene-1,3-dioxolanes) which are suitable as crosslinking agents in, for example, photocationic polymerisation systems.

The following practical examples illustrate the invention is greater detail:

EXAMPLE 1

A mixture prepared from 222 g (3 mol) of 90% hydroxyacetone, 331 g (3 mol) of 3-chloro-1,2-propanediol and 1 g of p-toluenesulfonic acid, hereinafter abbreviated as "p-TSA" is boiled in a water separator with 200 ml of cyclohexane as entraining agent. Once approx. 82 ml of water have separated, 2 g of potassium carbonate are added, the cyclohexane is removed and the remainder fractionated. 2-Methyl-2-hydroxymethyl-4-chloromethyl-1,3-dioxolane boils at 128° C. (1500 Pa); yield: 390 g (78%). IR: 3401 cm$^{-1}$ (—OH); MS: m/e=153/151 (M−15), 137/135, 117, 93, 75, 58, 43.

112 g of potassium tert.-butoxide are dissolved in 400 ml of dry THF and 145 g (0.87 mol) of the above product are slowly added dropwise thereto in such a manner that the reaction temperature does not exceed 50° C. The mixture is stirred overnight at room temperature, the THF is as far as possible removed by distillation and the residue is combined with 200 ml of water. The organic phase is separated, the aqueous phase extracted twice with 50 ml portions of toluene and the organic phases combined. After drying over Na$_2$SO$_4$, the product is fractionated. 48 g (42%) of 2-methyl-2-hydroxymethyl-4-methylene-1,3-dioxolane are obtained. Bp.: 90° C. (1500 Pa); IR: 1688 cm$^{-1}$ (double bond), 3468 cm$^{-1}$ (—OH); MS: m/e=130 (M$^+$), 99, 57, 43.

EXAMPLE 2

A mixture prepared from 191 g (1.87 mol) of 2,2-dimethyl-3-hydroxypropanol, 220 g (2 mol) of 3-chloro-1,2-propanediol and 200 ml of cyclohexane as entraining agent is boiled in a water separator. Once approx. 33 ml of water have separated, the cyclohexane is removed and the remainder fractionated. 2-(1-hydroxy-2-methylpropan-2-yl)-4-chloromethyl-1,3-dioxolane boils at 74° C. to 76° C. (0.2 Pa); yield: 230 g (63%). IR: 3436 cm$^{-1}$ (—OH); MS: m/e=195/193 (M$^+$), 164, 123/121, 115, 93, 75, 57, 43.

140 g (1.25 mol) of potassium tert.-butoxide are dissolved in 400 ml of dry THF and 190 g (0.98 mol) of the above product are slowly added dropwise thereto in such a manner that the temperature remains below 50° C. The mixture is stirred overnight at room temperature, the THF is as far as possible removed by distillation and the residue is combined with 200 ml of water. The organic phase is separated, dried over Na$_2$SO$_4$, and fractionated. 2-(1-hydroxy-2-methylpropan-2-yl)-4-methylene-1,3-dioxolane is obtained at a yield of 68 g (44%). Bp.: 52° C. (1 Pa); IR: 3387 cm$^{-1}$ (—OH), 1688 cm$^{-1}$ (double bond); MS: m/e=158 (M$^+$), 128, 102, 85, 72, 57, 43.

EXAMPLE 3

In a similar manner to the preceding Examples, 92.5 g (1 mol) of chloroacetone and 110.5 g (1 mol) of 3-chloro-1,2-propanediol are boiled together in a water separator with 0.5 g of p-TSA and 150 ml of cyclohexane. Once the equivalent quantity of water has separated, the cyclohexane is removed and the residue fractionated. 162 g (87%) of 2,4-bis(chloromethyl)-2-methyl-1,3-dioxolane are obtained. Bp.: 98° C. to 102° C. (1500 Pa); IR: acetal bands at 1120 cm$^{-1}$, 1098 cm$^{-1}$, 1053 cm$^{-1}$, MS: m/e=169 (M−15), 135, 106, 93, 75, 57, 49, 43.

130 g (0.7 mol) of the above product are slowly added dropwise to a solution of 95 g (0.85 mol) of potassium tert.-butoxide in 350 ml of dry THF in such a manner that the temperature does not exceed 50° C. Stirring is then continued for 3 hours at this temperature. Once the ether has been removed, the batch is taken up in 400 ml of water and extracted with acetic ester. The organic phase, which is then dried over Na$_2$SO$_4$, is evaporated and fractionated. 78 g (74%) of 2-chloromethyl-2-methyl-4-methylene-1,3-dioxolane are obtained: Bp.: 64° C. (1500 Pa); IR: 1689 cm$^{-1}$ (double bond, vinyl ether); MS: m/e=148 (M$^+$), 133 (M−15), 113, 106, 99, 92, 77, 57, 49, 43.

EXAMPLE 4

In a similar manner to the preceding Examples, 65 g (0.5 mol) of ethyl acetoacetate are heated together with 55 g (0.5 mol) of 3-chloro-1,2-propanediol and 0.2 g of p-TSA in a water separator. 100 ml of hexane act as entraining agent. Once 9 ml of water have separated, the reaction mixture is washed with 100 ml of water, to which 1 g of NaOH is added, dried over Na$_2$SO$_4$ and fractionated. 80 g (72%) of 2-methyl-2-ethoxycarbonylmethyl-4-chloromethyl-1,3-dioxolane are obtained. Bp.: 124° C. (1500 Pa); IR: 1736 cm$^{-1}$ (C=O, ester); MS: m/e=207 (M−15), 181, 173, 157, 144, 135, 115, 99, 75, 57, 43.

77 g (0.34 mol) of the above product are added dropwise at room temperature to a solution of 50.5 g (0.45 mol) of tert.-BuOK in 200 ml of dry THF in such a manner that the temperature remains below 30° C. After stirring overnight at room temperature, the batch is poured into 800 ml of iced water, extracted with diethyl ether and the organic phase dried over Na₂SO₄. After fractional distillation, 40 g (64%) of 2-methyl-2-ethoxycarbonylmethyl-4-methylene-1,3-dioxolane are obtained. Bp.: 90–92° C. (1500 Pa); IR: 1713 cm⁻¹ (C=O, ester), 1626 cm⁻¹ (double bond, vinyl ether); MS: m/e=186 (M⁺), 130, 113, 102, 84, 69, 57, 43.

Under certain circumstances, 2-ethoxycrotonic acid ethyl ester may occur as a secondary product (MS: m/e=158 (M⁺), 143, 130, 113, 85, 69, 58, 43).

EXAMPLE 5

27.2 g (0.4 mol) of sodium methoxide are initially introduced into 300 ml of DMF at approx. 40° C. and stirred. A mixture of 26 g (0.2 mol) of ethyl acetoacetate and 43 g (0.2 mol) of 1,4-dibromobutane is slowly added dropwise to this suspension and the reaction mixture is stirred for approx. 24 hours at this temperature. Towards the end of the reaction, the temperature may optionally be raised to 90° C. for a further hour. The precipitated sodium bromide is filtered out, the DMF removed and the residue fractionated. 29 g (78%) of 1-acetyl-1-cyclopentanecarboxylic acid ethyl ester are obtained. Bp.: 136° C. (1500 Pa); IR: 1745 cm⁻¹ (C=O, ester), 1713 cm⁻¹ (C=O, ketone); MS: m/e=142 (M–42), 114, 101, 96, 86, 67, 43.

14.5 g (78 mmol) of 1-acetyl-1-cyclopentanecarboxylic acid ethyl ester are boiled in a water separator together with 8.7 g (78 mmol) of 3-chloro-1,2-propanediol, 0.1 g of p-toluenesulfonic acid and 60 ml of toluene until no further water is separated. The mixture is then washed with weakly alkaline water, dried over sodium sulfate and the solvent removed. The crude yield of the corresponding ketal is 17.4 g (81%). IR: 1718 cm⁻¹ (C=O); MS: m/e=261 (M–15), 233, 209, 187, 135, 111, 95, 75, 67, 43.

11.2 g of tert.-BuOK are then initially introduced into a conical flask in 60 ml of dry THF and 17.4 g (63 mmol) of the chloromethyl compound are added dropwise such that the temperature remains below 40° C. Stirring is continued at room temperature for 8 hours, before the batch is poured into 200 ml of iced water and extracted with diethyl ether. The extract is dried over sodium sulfate and the ether stripped out. 2-Methyl-2-(1-cyclopentylcarboxylic acid ethyl ester-1-yl)-4-methylene-1,3-dioxolane is obtained in a crude yield of 11 g (72%). IR: 1724 cm⁻¹ (C=O, ester), 1687 cm⁻¹ and 1624 cm⁻¹ (vinyl ether); MS: m/e=240 (M⁺), 222, 185, 149, 114, 99, 67, 55, 43.

EXAMPLE 6

124 g (1 mol) of chloroacetaldehyde dimethyl acetal and 110 g (1 mol) of 3-chloro-1,2-propanediol are heated together with 0.3 g p-TSA and the resultant methanol removed by distillation. Once 32 g of methanol have passed over, the reaction mixture is washed with weakly alkaline water, the organic phase separated and dried over Na₂SO₄. After fractionation, 160 g (93%) of 2,4-bis(chloromethyl)-1,3-dioxolane are obtained. Bp.: 98° C. (1500 Pa); IR: 1191, 1049, 1007 cm⁻¹ (acetal); MS: m/e=169 (M–1), 140, 123, 121, 105, 93, 77, 75, 63, 57.

56 g (1 mol) of KOH are dissolved in 300 ml of isopropanol with heating and then 107 g (0.63 mol) of the above product are slowly added dropwise at 60° C. The mixture is then heated to boiling. After approx. 6 hours, the batch is poured into 1000 ml of iced water, extracted with diethyl ether, the extract dried over Na₂SO₄ and the ether removed. After fractionation through a 20 cm packed column, 60 g (71%) of 2-chloromethyl-4-methylene-1,3-dioxolane are obtained. Bp.: 56 to 58° C. (1500 Pa); IR: 1691 cm⁻¹ (double bond, vinyl ether); MS: m/e=134 (M⁺), 85, 76, 57, 49, 42.

Alternatively, elimination may proceed as follows: 60 g (1.5 mol) of NaOH pellets are initially introduced into a sufficiently large flask and 171 g (1 mol) of 2,4-bis(chloromethyl)-1,3-dioxolane are added. The mixture is carefully heated in an oil bath under a membrane pump vacuum with thorough stirring and the product is removed by distillation as a mixture with the water formed in the reaction. The 2-chloromethyl-4-methylene-1,3-dioxolane obtained in this manner is then dried over Na₂SO₄ and filtered. A second distillation stage is not generally necessary. Yield: 140 g (82%).

EXAMPLE 7

A mixture of 100 g (0.69 mol) of laevulinic acid ethyl ester, 76 g (0.69 mol) of 3-chloro-1,2-propanediol, 0.3 g of p-toluenesulfonic acid and 100 ml of toluene are heated in a water separator until no further water passes over. The toluene is then removed and the residue fractionated. 2-Methyl-2-(propionic acid ethyl ester-3-yl-)-4-chloromethyl-1,3-dioxolane is obtained in a yield of 95 g (58%). Bp.: 88° C. to 90° C. (1.5 Pa); IR: 1735 cm⁻¹ (C=O, ester); MS: m/e=221 (M–15), 191, 158, 147, 135, 113, 99, 75, 55, 43.

82 g (0.35 mol) of the chloromethyl compound are added dropwise to a solution of 45 g (0.4 mol) of tert.-BuOK in 200 ml of THF such that the temperature remains below 40° C. After the dropwise addition, the mixture is stirred for a further 3 hours at approx. 40° C., then cooled to room temperature and worked up using water. After extraction with petroleum ether and drying (Na₂SO₄), the solvent is separated and the residue fractionated. 2-Methyl-2-(propionic acid ethyl ester-3-yl)-4-methylene-1,3-dioxolane is obtained in a yield of 45 g (56%). Bp.: 50° C. (1 Pa); IR: 1735 cm⁻¹ (C=O, ester), 1687 cm⁻¹ vinyl ether); MS: m/e=200 (M⁺), 185, 155, 129, 111, 99, 71, 55, 43.

What is claimed is:

1. 4-Methylene-1,3-dioxolanes of the general formula I

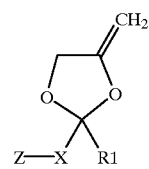

in which R1 denotes hydrogen or alkyl, X is C₁–C₁₈ alkylene, cycloalkylene, arylalkylene, —CH₂(OCH₂CH₂)ₙ— or —CH₂(OCH(CH₃)CH₂)ₙ—, in which n is an integer from 1 to 100, and Z means a functional group selected from among —OH, —COOR' and —OCOR', in which R' denotes hydrogen or C₁–C₈ alkyl.

2. 4-Methylene-1,3-dioxolanes according to claim 1, selected from the group consisting of 2-methyl-2-hydroxymethyl-4-methylene-1,3-dioxolane, 2-(1-hydroxymethyl-2-methylpropan-2-yl)-4-methylene-1,3-dioxolane, 2-methyl-2-ethoxycarbonylmethyl-4-methylene-1,3-dioxolane, 2-methyl-2-(1-cyclopentenylcarboxylic acid ethyl ester-1-yl)-4-methylene-1,3-dioxolane and 2-methyl-2-propionic acid ethyl ester-3-yl)-4-methylene-1,3-dioxolane.

3. 4-Chloromethyl-1,3-dioxolanes of the general formula II

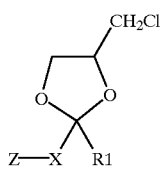

in which R1 denotes hydrogen or alkyl, X is $C_1$–$C_{18}$ alkylene, cycloalkylene, arylalkylene, —$CH_2(OCH_2CH_2)_n$— or —$CH_2(OCH(CH_3)CH_2)_n$—, in which n is an integer from 1 to 100 and Z means a functional group selected from among —OH and —OCOR', in which R' denotes hydrogen or $C_1$–$C_8$ alkyl.

4. 4-Chloromethyl-1,3-dioxolanes selected from the group consisting of 2-methyl-2-hydroxymethyl-4-chloromethyl-1,3-dioxolane, 2-(1-hydroxymethyl-2-methylpropan-2-yl)-4-chloromethyl-1, 3-dioxolane, 2-methyl-2-ethoxycarbonylmethyl-4-chloromethyl-1, 3-dioxolane, 2-methyl-2-ethoxycarbonylmethyl-4-chloromethyl-1, 3-dioxolane, 2-methyl-2-(1-cyclopentenylcarboxylic acid ethyl ester-1-yl)-4-chloromethyl-1, 3-dioxolane and 2-methyl-2-(propionic acid ethyl ester-3-yl)-4-chloromethyl-1,3-dioxolane.

5. A process for the production of the 4-methylene-1,3-dioxolanes according to claim 1, which comprises the steps of treating 4-chloromethyl-1,3-dioxolanes of the general formula II

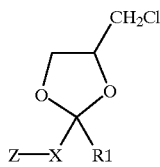

in which R1, X and Z are defined as in formula I, with a base at a temperature of 0° C. to 150° C. and isolating the reaction product.

6. A process according to claim 5, wherein the treatment step is performed at a temperature of 15° C. to 60° C.

7. A process according to claim 5, wherein treatment is performed in the presence of a solvent.

8. A process according to claim 7, wherein the solvent used is one which is a good solvent for the base.

9. A process according to claim 5, wherein the base used is potassium tert.-butoxide.

10. A process for the production of the 4-chloromethyl-1,3-dioxolanes according to claim 3, which comprises the steps of reacting aldehydes or ketones of the general formula III

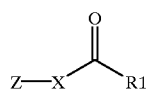

in which R1, X and Z are defined as in the formula II, with 3-chloro-1,2-propanediol and removing the resultant water of reaction.

11. A process according to claim 10, wherein the reacting step is performed in the presence of a catalyst.

12. A process according to claim 10, wherein an entraining agent is used.

13. A process for the production of the 4-chloromethyl-1,3-dioxolanes according to claim 3, which comprises the steps of treating acetals or ketals of the general formula IV

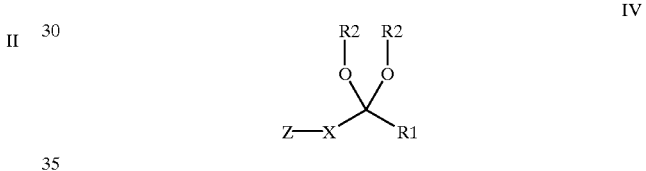

in which R1, X and Z are defined as in formula II and R2 denotes methyl or ethyl, with 3-chloro-1,2-propanediol in the presence of an acidic catalyst at a temperature of 25° C. to 150° C. and removing the resultant alcohol by distillation.

* * * * *